(12) United States Patent
Mortensen

(10) Patent No.: US 10,182,880 B2
(45) Date of Patent: Jan. 22, 2019

(54) ATTACHMENT AND COVER FOR AN ELECTRONIC IDENTIFICATION TAG

(71) Applicant: Caretag Surgical ApS, Horsholm (DK)

(72) Inventor: Soren Bilsoe Mortensen, Espergaerde (DK)

(73) Assignee: CARETAG SURGICAL APS, Horsholm (DK)

( * ) Notice: Subject to any disclaimer, the term of this patent is extended or adjusted under 35 U.S.C. 154(b) by 28 days.

(21) Appl. No.: 15/103,840

(22) PCT Filed: Dec. 11, 2014

(86) PCT No.: PCT/EP2014/077453
§ 371 (c)(1),
(2) Date: Jun. 10, 2016

(87) PCT Pub. No.: WO2015/086775
PCT Pub. Date: Jun. 18, 2015

(65) Prior Publication Data
US 2016/0296299 A1    Oct. 13, 2016

(30) Foreign Application Priority Data

Dec. 11, 2013   (EP) ..................................... 13196686
Sep. 4, 2014    (DK) ................................. 2014 70539

(51) Int. Cl.
*A61B 90/98* (2016.01)
*A61B 90/90* (2016.01)
(Continued)

(52) U.S. Cl.
CPC .............. *A61B 90/98* (2016.02); *A61B 90/90* (2016.02); *B29C 65/02* (2013.01); *B29C 65/48* (2013.01);
(Continued)

(58) Field of Classification Search
CPC ......... B29C 65/02; B29C 65/48; B29C 65/70; B29L 2007/004; A61B 90/90; A61B 90/98
See application file for complete search history.

(56) References Cited

U.S. PATENT DOCUMENTS 5,365,655 A    11/1994  Rose
5,420,757 A    5/1995   Eberhardt et al.
(Continued)

FOREIGN PATENT DOCUMENTS

EP    1020814 A2 *  7/2000  ....... G06K 19/07745
EP    1020814 A2     7/2000
(Continued)

OTHER PUBLICATIONS

Machine translation of WO 2011054355 A2.*
(Continued)

*Primary Examiner* — Vishal I Patel
(74) *Attorney, Agent, or Firm* — Knobbe, Martens, Olson & Bear, LLP

(57) ABSTRACT

Disclosed are an apparatus and a method for attaching an identification tag to a solid surface and protecting the identification tag. The identification tag has a first surface and a second surface opposite the first surface. The method comprises: positioning the first surface of the identification tag in contact with an attachment site of the solid surface; applying a predetermined amount of a first adhesive substance on the second surface, the first adhesive substance being plastic during application and curable after application, the first adhesive substance having a first viscosity at the time of application; forming the first adhesive substance, such that the first adhesive substance covers the identifica-
(Continued)

tion tag and abut a part of the solid surface circumscribing the identification tag; and curing the first adhesive substance.

21 Claims, 7 Drawing Sheets

(51) Int. Cl.
*B29C 65/02* (2006.01)
*B29C 65/48* (2006.01)
*B29C 65/70* (2006.01)
*B29L 7/00* (2006.01)

(52) U.S. Cl.
CPC ......... *B29C 65/70* (2013.01); *B29L 2007/004* (2013.01)

(56) References Cited

U.S. PATENT DOCUMENTS

| | | | |
|---|---|---|---|
| 6,366,206 | B1 | 4/2002 | Ishikawa et al. |
| 2003/0179150 | A1 | 9/2003 | Adair et al. |
| 2006/0145871 | A1 | 7/2006 | Donati et al. |
| 2007/0244470 | A1 | 10/2007 | Barker, Jr. et al. |
| 2008/0131623 | A1 | 6/2008 | Zhang et al. |
| 2008/0211087 | A1 | 9/2008 | Mueller-Hipper et al. |
| 2008/0238631 | A1 | 10/2008 | Blake et al. |
| 2010/0079290 | A1 | 4/2010 | Phaneuf |
| 2010/0176925 | A1* | 7/2010 | Tethrake ............... A61B 90/00 340/10.1 |
| 2014/0014731 | A1 | 1/2014 | Huang |
| 2014/0088570 | A1 | 3/2014 | Sergeant |

FOREIGN PATENT DOCUMENTS

| | | |
|---|---|---|
| EP | 1020814 A3 | 10/2002 |
| EP | 2357705 A1 | 8/2011 |
| FR | 2918769 A1 | 1/2009 |
| FR | 2974496 A1 | 11/2012 |
| JP | H10147088 A | 6/1998 |
| WO | 2007/074394 A2 | 7/2007 |
| WO | 2009/049011 A1 | 4/2009 |
| WO | 2010003190 A1 | 1/2010 |
| WO | 2010003190 A8 | 1/2010 |
| WO | 2011054355 A2 | 5/2011 |
| WO | 2011054355 A3 | 5/2011 |

OTHER PUBLICATIONS

Danish Office Action with Search Report for Application No. PA201470539, dated Oct. 24, 2014, 8 pages.
International Search Report dated May 11, 2015, issued in PCT Application No. PCT/EP2014/077453, filed Dec. 11, 2014 (4 pages).
Extended European Search Report dated Jun. 11, 2014, issued in European Application No. 13196686.3 (7 pages).

* cited by examiner

ATTACHMENT AND COVER FOR AN ELECTRONIC IDENTIFICATION TAG

CROSS REFERENCE TO RELATED APPLICATION

This application is the U.S. National Phase Application under 35 U.S.C. § 371 of International Application No. PCT/EP2014/077453, filed Dec. 11, 2014, designating the U.S. and published as WO 2015/086775 on Jun. 18, 2015, which claims the benefit of European Patent Application No. EP 13196686.3, filed Dec. 11, 2013 and Denmark Patent Application No. PA201470539, filed Sep. 4, 2014. These prior applications and any and all applications for which a foreign or a domestic priority is claimed and is/are identified in the Application Data Sheet filed herewith, are hereby incorporated by reference in their entirety under 37 C.F.R. § 1.57.

TECHNICAL FIELD

The present invention relates to attachment of an identification tag, such as an electronic identification tag, such as an RFID tag, to a solid material, such as medical equipment such as utensils, disposables and/or surgical instruments. Especially, the present invention relates to attachment and cover for an identification tag attached to surgical instruments for registration before and after an operation, or before and after sterilization.

BACKGROUND

In an operating room, both certain surgical instruments and a certain number of instruments may be needed to perform a surgical procedure. Typically the instruments brought into the operating room prior to an operation is counted and registered manually, to be certain that the right amount and correct instruments are available for operation. After completion of the operation, the instruments are again counted and registered manually, to ensure that no instruments are missing.

Manually registering and counting of equipment, before and after a surgery, is both time consuming and ineffective. Further, the consequence of errors may in a worst case scenario pose a life threatening situation for the patient.

Other situations exist where medical instruments need to be registered, and where a more efficient procedure will be beneficial, e.g. before and after sterilization, in or out of maintenance etc.

Providing the available instruments with an identification tag, such as an electronic identification tag, such as an RFID tag, it is in theory possible, within a couple of seconds, to read the presence of all identification tags, and thus all instruments present in a defined space. Identification tags may be in sizes of millimeters, and may be reliably read from a distance of a couple of meters. However, these sizes and ranges are continuously improved.

However, instruments are seldom manufactured with identification tags and several problems occur when attaching an identification tag to an instrument.

The identification tag may provide undue protrusions or sharp edges. This is especially a problem in surgical instruments for use in an operating room, the sharp edges may cause rubber gloves to be torn and pose a hygiene risk, both for the surgeon and the patient.

Further, cleaning, washing, and sterilization of the instruments may cause the identification tag to be separated from the instrument. Especially, an identification tag may be in risk of impacts by other instruments during washing, causing separation from the instrument and/or damage of the identification tag.

Further, sharp edges may pose adverse grooves that may be difficult to clean.

Prior art exists wherein encapsulation of semiconductors have been proposed. For example, U.S. Pat. No. 5,365,655 disclose a method of making electronic modules for electronic memory cards and to electronic modules. Wherein an insulating resin forms an encapsulation for a semiconductor chip placed on a face of the metal strip. However, U.S. Pat. No. 5,365,655 apply a mold surrounding the semiconducter and therefore cannot be directly applied to provide attachment and cover of an identification tag applied to an existing solid surface, such as solid surface of a medical instrument.

US 2010/0176925 disclose methods for providing surgical instruments with an RFID transponder tag, wherein the tag may be adhered to, embedded, or potted within a portion of the instrument. However, US 2010/0176925 does not disclose effective ways of covering an identification tag while maintaining the shape and structure of the medical instrument.

WO 2011/054355 discloses a method for applying an RFID chip, on a medical instrument. The RFID chip is provided with a protective layer by applying a mixture of polymerizable acrylates or methacrylates or a solid on top of the RFID chip placed on the medical instrument. However, WO 2011/054355 does not provide a method which allows for an automated process.

SUMMARY

There is a need for a method of attaching an identification tag, such as an electronic identification tag, such as an RFID tag to a solid surface, such as a solid surface of a part to identify such as an instrument, e.g. a surgical instrument, and wherein the method provides a protection to the identification tag and the attachment between the part to identify and the identification tag.

It is realized that if the identification tag has surfaces perpendicular to an attachment surface, wherein the attachment surface is the surface being attached to the solid surface, upon impact of the surface perpendicular to the attachment surface the force of the impact facilitates removal of the tag.

Therefore, a method and an assembly are sought that removes or at least reduces surfaces which upon impact facilitate removal of the identification tag. Further, a method and an assembly are sought that removes or at least reduces sharp edges of an identification tag attached to a solid surface.

Accordingly, a method is provided, a method for attaching an identification tag to a solid surface, such as a solid surface of an instrument or a surgical instrument such as a lancet or a scissor or a clamp, such as a metal surface, and protecting the identification tag. The identification tag has a first surface, such as a first outward surface, and a second surface, such as a second outward surface, opposite the first surface. The method comprises: positioning the first surface of the identification tag in contact with an attachment site of the solid surface; applying a predetermined amount of a first adhesive substance on the second surface, the first adhesive substance being plastic. i.e. moldable, during application and curable, i.e. hardens to permanent form, after application, the first adhesive substance having a first viscosity at the time of application; forming the first adhesive substance, such that the first adhesive substance covers the identification tag and abut a part of the solid surface circumscribing the identification tag; and curing the first adhesive substance.

Also disclosed is an apparatus for attaching an identification tag to a solid surface, such as a solid surface of an instrument or a surgical instrument such as a lancet or a scissor or a clamp, such as a metal surface, and protecting the identification tag. The apparatus comprises: positioning means configured to position a first surface of the identification tag in contact with an attachment site of the solid surface; application means configured to apply a predetermined amount of a first adhesive substance on a second surface of the identification tag opposite the first surface; the first adhesive substance being plastic during application and curable after application, the first adhesive substance having a first viscosity at the time of application; forming means configured to form the first adhesive substance; and first curing means configured to cure the first adhesive substance. The forming means are configured to form the first adhesive substance such that the first adhesive substance covers the identification tag and abut a part of the solid surface circumscribing the identification tag.

Curing is a term in polymer chemistry and process engineering that refers to the toughening or hardening of a polymer material by cross-linking of polymer chains, brought about by chemical additives, ultraviolet radiation, electron beam or heat. When using the word "curing" in the present application, the word should include all hardening and toughening processes regardless of which chemical reaction and/or physical process is behind. For example, a material, such as an adhesive substance, such as the first adhesives substance, may be plastic and have a first viscosity at the time of application. During curing, the adhesive substance hardens i.e. the viscosity increases relative to the first viscosity.

Also disclosed is an assembly, such as an assembly achieved by the disclosed method, the assembly comprising: a solid surface, such as a solid surface of an instrument or a surgical instrument such as a lancet or a scissor or a clamp; an identification tag attached to the solid surface, the identification tag having a first surface and a second surface opposite the first surface, the first surface facing the solid surface; a first adhesive substance covering the second surface and an area of the solid surface circumscribing the identification tag; wherein the first adhesive substance is a plastic and curable material. After curing the first adhesive substance a smooth surface is formed covering the identification tag.

It is an advantage of the present invention that a smooth surface is applied on top of the identification tag. The smooth surface, formed by a cured adhesive substance, eliminates or at least reduces surfaces being perpendicular to the first surface. Further, the smooth surface eliminates or at least reduces sharp edges that are at risk of tearing plastic gloves. Finally, the smooth surface protects the identification tag.

A further advantage of the invention is that attachment of an identification tag to a non planar surface can be improved and strengthened.

An even further advantage of the invention is that attaching an identification tag to a solid surface and protecting the identification tag may be achieved using an automated process.

The attachment site might be pre-treated, e.g. polishing, cleaning, etc., but is otherwise not changed compared to the surface of an instrument not provided with an identification tag. Hence, material of the solid surface is not removed to provide an indentation or the like.

Thus, it is an even further advantage of the invention that attaching an identification tag may be performed on a solid surface without altering the solid surface. Thereby, properties, such as strength, weight, weight distribution, etc, of the solid surface and/or the element comprising the solid surface, is retained, or at least substantially retained. This is especially important in cases where the solid surface is a solid surface of a medical instrument. Thus, it is an advantage of the invention that an identification tag may be subsequently attached to an existing, and maybe medically approved, medical instrument.

It should be noted that the above mentioned advantages of the current invention is not an exhaustive list and there may be other advantages which are not described herein.

Applying the first adhesive substance on the second surface may comprise applying a predetermined amount of the first adhesive substance on the second surface. The predetermined amount may be selected such that the first adhesive substance, at least upon forming the first adhesive substance, flows down along the external surfaces of the identification tag and completely cover the identification tag before curing. The predetermined amount may be selected such that the first adhesive substance is only situated on the second surface before forming the first adhesive substance.

The predetermined amount and viscosity of the first adhesive substance may be adapted in such a way that the first adhesive substance, upon forming of the first adhesive substance, flows down along the external surfaces of the identification tag and completely cover the identification tag before curing. How the first substance is adapted will depend on the chosen substance, normally the process may be controlled by temperature and e.g. by admixing solvents or plasticizers.

An adhesive substance suitable for the present invention, such as the first adhesive substance and/or a second adhesive substance, may be configured to withstand repeated sterilization procedures at high temperature e.g. autoclaving, after the adhesive substance has cured.

Forming the first adhesive substance may comprise subjecting the first adhesive substance to an energy intensity, such as a first energy intensity, for a first duration. The first energy intensity and/or the first duration may be selected such that viscosity of the first adhesive substance is decreased relative to the first viscosity. An energy intensity, such as the first energy intensity and/or a second energy intensity, may be a temperature, e.g. in atmospheric air, such as a constant temperature. Alternatively or additionally, an energy intensity, such as the first energy intensity and/or the second energy intensity, may be a radiation flux, e.g. microwave radiation, ultraviolet radiation, and/or infrared radiation.

Decreasing viscosity of the first adhesive substance may be performed differently depending on the exact type of adhesive substance. For example, the first energy intensity may be 100 degrees celcius in atmospheric air, and/or the first duration may be a fixed duration, such as a fixed duration between 1 min and 10 min.

Curing the first adhesive substance may comprise subjecting the first adhesive substance to an energy intensity, such as the first energy intensity and/or the second energy intensity, for a second duration. The second energy intensity may be similar to the first energy intensity. Alternatively, the first energy intensity and the second energy intensity may be different.

Curing of the first adhesive substance and/or of a second adhesive substance may be performed differently depending on the exact type of adhesive substance. For example, the second energy intensity may be 100 degrees celcius in atmospheric air, and/or the second duration may more than 10 minutes and/or a fixed duration, such as a fixed duration of more than 10 minutes, such as between 50 min and 60 min.

The first adhesive substance may have certain properties, e.g. viscosity of the first adhesive substance may initially decrease and subsequently increase relative to the first viscosity when subjecting the first adhesive substance to an energy intensity, such as the first energy intensity. Such properties may be beneficial, since subjecting the first adhesive substance to an energy intensity, such as the first energy intensity may provide that the first adhesive substance initially decrease viscosity and thereby, e.g. due to gravity, spread over the identification tag and cover the sides of the identification tag, and continued subjection of the first adhesive substance to the energy intensity eventually cures, i.e. hardens, the first adhesive substance. Thereby, the same energy intensity, e.g. the same temperature, may be used for forming the first adhesive substance, by decreasing viscosity, and for curing the first adhesive substance.

The first surface of the identification tag being positioned in contact with the solid surface may comprise a substance, such as an adhesive substance, to form the contact between the first surface of the identification tag and the solid surface.

Positioning the first surface of the identification tag in contact with the solid surface may comprises applying a second adhesive substance between the solid surface and the first surface.

An adhesive substance, such as the second adhesive substance may be applied between the solid surface and the first surface. The provision of a second adhesive substance between the solid surface and the first surface may provide for the identification tag to be more solidly bound to the first surface, providing an increased resistance to wear and tear. The second adhesive substance may be applied prior to positioning the first surface of the identification tag in contact with the solid surface.

The second adhesive substance may be applied on the solid surface, and/or the second adhesive substance may be applied to the first surface, and/or the second adhesive substance may be squeezed into a gap between the solid surface and the first surface.

Positioning the first surface of the identification tag in contact with the solid surface may comprise positioning the first surface of the identification tag in contact with the second adhesive substance applied to the solid surface.

The second adhesive substance may be, at least initially, cured prior to applying the first adhesive substance on the second surface. For example, positioning the first surface of the identification tag in contact with the solid surface may comprise initially curing the second adhesive substance, e.g. prior to applying the first adhesive substance on the second surface.

Initially curing the second adhesive substance may comprise curing of the second adhesive substance for an initial duration. The initial duration may be minimum 0.01 seconds or minimum 0.5 seconds or minimum 1 second and/or less than 30 seconds, such as less than 10 seconds, such as less than 5 seconds, such as less than 2 seconds, such as less than 1 second.

Curing and/or initially curing the second adhesive substance may comprise subjecting the second adhesive substance to an energy intensity, such as an initial energy intensity, the first energy intensity, and/or the second energy intensity. The initial energy energy intensity may be similar to the first energy intensity and/or the second energy intensity.

An energy intensity, such as the initial energy intensity, may be a temperature, e.g. in atmospheric air, such as a constant temperature. Alternatively or additionally, an energy intensity, such as the initial energy intensity may be a radiation flux, e.g. microwave radiation, ultraviolet radiation, and/or infrared radiation. For example, curing and/or initially curing the second adhesive substance may be performed by applying heat and/or radiation, such as visible light and/or ultraviolet light and/or infrared light, to the second adhesive substance. Initially curing the second adhesive substance may be performed by heating the solid surface and/or the element comprising the solid surface.

In some applications, e.g. when attaching an identification tag to a medical instrument, precise positioning of the identification tag is crucial to the reliability of reading the identification tag. Therefore, it is important that the positioning of the identification tag may be controlled.

Applying and/or, at least initially, curing the second adhesive substance between the solid surface and the first surface may prevent movement of the identification tag relative to the solid surface when providing the first adhesive substance. Thereby providing a possibility to attach and protect the identification tag using an automated process. For example, a machine may be provided which automatically apply the necessary adhesives, such as the first adhesive and/or the second adhesive substance. Thus, the initial duration may be long enough to immobilize the identification tag relative to the solid surface. Also the initial duration may be short to decrease total process time.

The initial duration may be the duration and/or period for initially curing of the second adhesive substance. The initial duration may be shorter than a duration for curing the first and/or second adhesive substance, such as the second duration. The initial duration may be less than 20 seconds, such as less than 10 seconds, such as less than 5 seconds, such as less than 1 second.

The curing process when applying an initial curing may for example be outlined as:
  Step 1: Applying the second adhesive substance.
  Step 2: Curing the second adhesive substance for the initial duration, e.g. between 0.5-20 seconds.
  Step 3: Applying the first adhesive substance.
  Step 4: Curing the first and the second adhesive substance for the first and/or second duration, e.g. between 1 second 60 minutes.

Alternatively, the identification tag may be positioned directly on the solid surface. The first adhesive substance may provide the binding of the identification tag to the solid surface. Omitting the second adhesive may simplify the method, and hence, imply reduced costs.

The second adhesive substance may be the same type of adhesive substance as the first adhesive substance. It is an advantage that the first adhesive substance be the same, or the same type, as the second adhesive substance, to decrease the number of different substances and hence reduce costs. However, it may alternatively be beneficial to utilize different types of adhesive substances, to employ different properties.

The second adhesive substance and the first adhesive substance may cure concurrently. It may be beneficial, to save production time and to ease assembly, to cure both the first adhesive substance and the second adhesive substance concurrently. The first adhesive substance and the second adhesive substance may be cured by the same curing process. For example, the first adhesive substance and/or the second adhesive substance may be cured by applying a curing agent, such as the first and/or second energy intensity, such as heat and/or ultraviolet radiation, to the first adhesive substance and/or the second adhesive substance, respectively.

An adhesive substance, such as the first adhesive substance or the second adhesive substance, is a plastic material in the sense that it can be molded or formed into a desired shape. The plastic material may alternatively be referred to as viscoelastic. The adhesive substance may additionally possess liquid properties, alternatively referred to as viscous. Further, an adhesive substance, such as the first adhesive substance or the second adhesive substance, has adhering properties and configured to bind together two surfaces and to resist subsequent separation of the two surfaces. Further, an adhesive substance, such as the first adhesive substance or the second adhesive substance, is a curable material in the sense that the substance will harden and the adhering property of the free surface is stopped.

It is to be noted that the adhesive substance, such as the first adhesive substance and/or the second adhesive substance, has first mechanical properties at the time of application, e.g. liquid, plastic, and/or adhesive, and second mechanical properties after curing, e.g. hard, smooth, and/or non adhesive.

An adhesive substance, such as the first adhesive substance and/or the second adhesive substance may be a substance of polymers and/or pre-polymers. The adhesive substance may be a thermosetting polymer which changes irreversibly into an infusible, insoluble polymer network by curing. The adhesive substance may be hardened and toughened during a curing process. Curing of the adhesive substance may induce polymers and/or pre-polymers of the adhesive substance to form cross-links.

The adhesive substance, such as the first adhesive substance and/or the second adhesive substance may be a glue e.g. an epoxy glue and/or a two component glue and/or a two-component epoxy glue. Epoxy glue contains a network of reactive pre-polymers and polymers which contains epoxide groups. During curing of the epoxy glue, the epoxy glue forms three-dimensional cross-linked thermoset structures.

Curing of an adhesive substance may be performed by exposing the adhesive substance to chemical additives, ultraviolet radiation, electron beams or heat. The curing of the first adhesive substance and/or the second adhesive substance may for example be induced or accelerated by applying heat to the respective adhesive substance. The curing may comprise exposing the adhesive substance to a predetermined temperature for a predetermined duration of time in an environment of a predetermined pressure. For example the curing may involve exposing the adhesive substance to 100 degrees celsius for 60 minutes at atmospheric pressure.

A two-component glue, such as a two-component epoxy glue, may be advantageous, as the curing process is initiated when mixing the two components, i.e. the initiation of the curing process can be controlled. This is an advantage when applying the first and/or second adhesive substance in an automated process. For example, applying the first adhesive substance on the second surface may comprise mixing, such as simoultaneous mixing, two components of the first adhesive substance.

The first and/or second adhesive substance may be pre-cured prior to applying the respective adhesive substance. Pre-curing may provide the adhesive substance in question to be more solid and less liquid, meaning that the adhesive substance will be more prone to retain its shape when molded. Further, pre-curing may provide easier application of the adhesive substance due to a reduced flow of the adhesive substance. For example, the second adhesive substance may be pre-cured prior to applying the second adhesive substance between the solid surface and the first surface.

The method may comprise identifying the attachment site on the solid surface, such as the attachment site for applying the second adhesive substance and/or for positioning the first surface of the identification tag. Identifying the attachment site may be performed prior to positioning the first surface of the identification tag in contact with the solid surface and/or prior to applying the second adhesive substance. The second adhesive substance may be applied to the identified attachment site. Positioning the first surface of the identification tag in contract with the solid surface may comprise positioning the first surface of the identification tag in contract with the solid surface at the attachment site and/or positioning the first surface of the identification tag in contact with the second adhesive substance applied to the attachment site.

In some applications, e.g. when attaching an identification tag to a medical instrument, precise positioning of the identification tag is crucial to the reliability of reading the identification tag. Furthermore, a desired attachment site may vary depending on the specific element and/or solid surface, e.g. an optimal attachment site may be known for a scissor and another optimal attachment site may be known for a lancet.

Identifying the attachment site may be performed with identification means, such as a visual detection unit, such as a camera.

Identifying the attachment site may comprise recognition of the solid surface, e.g. optical recognition, such as image recognition and/or pattern recognition, of the solid surface. Identifying the attachment site may comprise a table lookup and/or a database lookup, wherein the table and/or database comprise attachment site data of the solid surface and/or a plurality of solid surfaces including the solid surface. The attachment site data may comprise instructions for the attachment site on the solid surface. For example, the solid surface is recognized using optical recognition, such as image recognition or pattern recognition; a table and/or database lookup provides attachment site data for providing the attachment site on the solid surface.

Identifying the attachment site enhance the reliability of reading the identification tag, and furthermore provides consistent positioning of identification tags. Furthermore, identifying the attachment site provides an enhanced possibility of implementing the method by an automated process, e.g. an apparatus configured to perform the method.

A cover surface may be applied to the identification tag. The cover surface may cover the second surface of the identification tag and a part of the solid surface circumscribing the identification tag. The cover surface may be hard and smooth. The cover surface may be hard and smooth to deflect impacts from other objects, thereby preventing the identification tag from being separated from the solid surface. Further, a smooth cover surface prevents unintentional adhering to objects such as plastic gloves. The cover surface may be smooth in the sense of an absence of irregularities. The cover surface may be smoothened by mechanical polishing of the cover surface. The cover surface may be hard in the sense that it withstands deformations. On a Shore D scale, the hardness of the cover surface may be more than 60 D, or more than 70 D, or more than 80 D.

In some embodiments the cover surface is formed by the first adhesive substance. The first adhesive substance may form the cover surface when the first adhesive substance has been cured. The mechanical properties of the cover surface may be regarded as the mechanical properties of the first adhesive substance after curing.

Forming the first adhesive substance may comprise applying a concave surface of a mold such that the mold abuts a part of the solid surface circumscribing the identification tag.

The first adhesive substance may be formed by applying a mold over the identification tag and the first adhesive substance. The mold may comprise a concave surface. The concave surface may be applied over the identification tag, such that the concave surface encloses the identification tag and a circumference of the concave surface abuts a part of the solid surface circumscribing the identification tag. Thereby, the first adhesive substance may be distributed to partly or completely cover the identification tag and formed in accordance to the shape of the concave surface.

Forming the first adhesive substance may comprise removing the mold. The mold may be removed and the first adhesive substance may be cured to maintain the shape obtained from the concave surface.

In some embodiments, the cover surface may be formed by the mold. The first adhesive substance may be cured without removing the mold. The mold may be fastened to the identification tag and/or the solid surface. Curing the first adhesive substance without removing the mold may adhere the mold to the solid surface and/or the identification tag thereby an outer surface of the mold may form the cover surface of the identification tag. The outer surface of the mold may comprise a plurality of surfaces.

Further, the outer surface of the mold may be covered by a third adhesive substance after curing the first adhesive substance. The third adhesive substance may be applied in a state liquid enough to spread over the outer surface. The cover surface may thus be formed by the third adhesive substance. The third adhesive substance may be the same type of adhesive substance as the first adhesive substance and/or the second adhesive substance.

The mold may fit the identification tag and/or the solid surface. The mold may be constructed to fit the identification tag and the solid surface. The mold may be selected from a plurality of molds, wherein each of the plurality of molds fits a predetermined solid surface and/or identification tag. Forming the first adhesive substance may comprise selecting the mold to fit the combination of the identification tag and the solid surface. The mold may be adapted to fit the solid surface to account for curvatures of the solid surface. The mold may be adapted to fit the identification tag to account for different shapes and sizes of the identification tag.

A method of attaching and covering an identification tag may comprise constructing the mold. The construction of the mold may comprise constructing the mold to fit the identification tag and/or the solid surface Identification tags are of varying shapes and sizes e.g. depending on the manufacturer. The mold may be configured to fit the identification tag. Thereby, different size and shapes of identification tags are accounted for.

Further, the solid surface to attach the identification tag may vary, e.g. from one pad to identify to another, and the solid surface may not necessarily be a plane surface. The mold may be configured to fit the solid surface.

The mold may be single use. The mold may be disposed after use. The mold may be fastened to the identification tag and/or the solid surface as described above.

Application of the first adhesive substance may comprise applying a predetermined amount of the first adhesive substance. The predetermined amount of the first adhesive substance may be applied to the second surface of the identification tag, and/or the predetermined amount of the first adhesive substance may be applied to the concave surface of the mold. Alternatively, application of the first adhesive substance may comprise applying a first predetermined amount of the first adhesive substance to the concave surface of the mold and a second predetermined amount of the first adhesive substance to the second surface of the identification tag. A predetermined amount of the first adhesive substance may be determined to fit the size of the mold, such that there is enough adhesive substance to cover the identification tag, and little enough that the adhesive substance can be contained in the mold or to limit an excess amount of the first adhesive substance.

The concave surface of the mold may be coated with a substance to prevent the first adhesive substance and/or the second adhesive substance to adhere to the concave surface. The substance to prevent any of the adhesive substances to adhere to the concave surface may be applied each time prior to applying an adhesive substance to the concave surface, or it may be applied with a predetermined interval, such as every tenth time, every twentieth time or every fiftieth times. Alternatively the substance may be provided once to each mold.

Preventing the first adhesive substance from adhering to the concave surface, all a mold to be used a plurality of times.

The concave surface may contain means to provide a logo, company name, or another graphical element in the first adhesive substance. For example, the concave surface may be supplied with a protruding logo, which will leave an indented logo in the first adhesive substance.

It is envisaged that any embodiments or elements as described in connection with any one aspect may be used with any other aspects or embodiments, mutatis mutandis. For example, the apparatus as disclosed may comprise means configured to perform steps of the disclosed method.

Positioning means, configured to position the first surface of the identification tag in contact with an attachment site of the solid surface, may be a robotic arm, such as a first robotic arm. The positioning means may further be configured to apply a second adhesive substance between the solid surface and the first surface.

Application means configured to apply a predetermined amount of a first adhesive substance on the second surface may be a robotic arm, e.g. a second robotic arm and/or the first robotic arm. The application means may further be configured to apply a second adhesive substance between the solid surface and the first surface.

Forming means configured to form the first adhesive substance may be heating means, radiation means, and/or a mold and/or means to apply a mold. For example, forming means may comprise a robotic arm, e.g. a third robotic arm, the second robotic arm, and/or the first robotic arm.

Forming means may comprise viscosity alteration means configured to decrease viscosity of the first adhesive substance, e.g. by subjecting the first adhesive substance to a first energy intensity for a first duration. The first energy intensity and the first duration may be selected such that viscosity of the first adhesive substance is decreased relative to the first viscosity.

Curing means, such as the first curing means and/or second curing means, may be means for application of a curing agent, e.g. heat, radiation, and/or energy intensity. For example, the first curing means may be configured to cure the first adhesive substance, e.g. by subjecting the first adhesive substance to the second energy intensity for the second duration.

The apparatus may comprise heating means. The heating means may comprise and/or be the curing means, such as the first curing means, and/or the viscosity alteration means. For example, the heating means may perform both a viscosity alteration in relation to the forming of the first adhesive substance, and a curing in relation to the curing of the first and/or second adhesive substance.

The apparatus may comprise identification means configured to identify the attachment site on the solid surface, such as described earlier. The identification means may comprise a camera.

The apparatus may comprise preperation means configured to prepare the attachment site. Preferably, preparing the attachment site is performed without substantially altering the solid surface. Preperation of the attachment site may involve polishing and or cleaning, such as washing and/or desinfecting. The preperation means may comprise air blowing means, such as a nozzle, for blowing dirt off the attachment site.

The apparatus may comprise control means, such as a control unit, such as a processing unit. Control means may be configured to control the apparatus and/or other means of the apparatus.

The control means, such as the control unit, may be configured to control the positioning means to position the first surface of the identification tag in contact with the attachment site of the solid surface.

The control means, such as the control unit may be configured to control the application means to apply the predetermined amount of the first adhesive substance on the second surface The control means, such as the control unit may be configured to control the forming means to form the first adhesive substance.

The control means, such as the control unit may be configured to control curing means, such as the first curing means and/or the second curing means, e.g. to cure the first adhesive substance and/or the second adhesive substance.

The control means, such as the control unit may be configured to control the identification means.

The control means, such as the control unit, may be configured to control a curing process, such as the initial curing of the second adhesive substance and/or the curing process of the first adhesive substance and optionally the second adhesive substance.

The control means, such as the control unit, may be configured to control the timing of the curing process and/or the application of a curing agent, such as the first and/or second energy intensity, such as heat and/or ultraviolet radiation.

An identification tag is preferably an electronic identification tag such as a radio frequency identification (RFID) tag, a near field communication (NFC) tag, or a similar identification tag based on wireless transmission of electromagnetic signals and unique identification of the tag.

BRIEF DESCRIPTION OF THE DRAWINGS

The above and other features and advantages of the present invention will become readily apparent to those skilled in the art by the following detailed description of exemplary embodiments thereof with reference to the attached drawings, in which.

DETAILED DESCRIPTION

Figure 1:
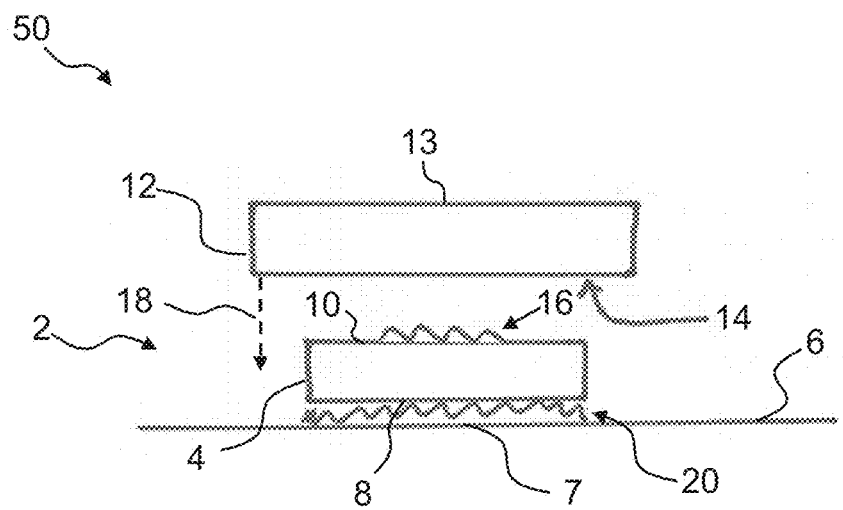
FIG. 1 schematically illustrates an exemplary step of a method.

In the following "generally" means observations or examples which are applicable for all embodiments.

The figures are schematic and simplified for clarity, and they merely show details which are essential to the understanding of the invention, while other details have been left out. Throughout, the same reference numerals are used for identical or corresponding parts.

FIG. 1 schematically illustrates an exemplary step 50 of a method of creating an assembly 2. The assembly 2 comprises an identification tag 4, a solid surface 6, and a first adhesive substance 16.

The identification tag 4 comprises a first surface 8 and a second surface 10. The first surface 8 is facing the solid surface 6. The solid surface 6 is a solid surface of a part to identify, e.g. an instrument, such as a surgical instrument, such as a lancet, a scissor, or a clamp.

The first surface 8 of the identification tag 4 is positioned in contact with an attachment site 7 of the solid surface 6.

A predetermined amount of the first adhesive substance 16 is applied to the second surface 10 of the identification tag 4. The first adhesive substance 16 is a predetermined amount of the first adhesive substance 16 applied to the second surface 10.

The first adhesive substance 16 is to be formed such that the first adhesive substance 16 covers the identification tag 4 and abut a part of the solid surface 6 circumscribing the identification tag.

In one exemplary embodiment, a mold 12 comprising a concave surface 14 is applied over the identification tag 4. The mold 12 is applied such that concave surface 14 is placed on top of the second surface 10 and the first adhesive substance 16. The mold 12 is moved downwards 18 over the identification tag 4, such that the mold abuts a part of the solid surface 6 circumscribing the identification tag 4. A certain pressure may be applied to the mold 12 in the downward direction 18, such that the first adhesive substance 16 is spread over the identification tag 4.

Generally, when joined together the concave surface 14 providing an opening in the mold 12 together with the solid surface 6 of a part to identify create a closed or semi-closed space wherein the identification tag 4 and the first adhesive substance 16 and optionally the second adhesive substance are positioned during application. "Semi-closed" means that there are openings e.g. allowing a surplus of adhesive to escape.

In another exemplary embodiment, the first adhesive substance 16 is formed by subjecting the first adhesive substance 16 to a first energy intensity such that viscosity of the first adhesive substance 16 is decreased, and the first adhesive substance flows to cover the identification tag 4 and abut a part of the solid surface 6 circumscribing the identification tag.

Subsequently, i.e. after forming the first adhesive substance, the first adhesive substance 16 is cured, e.g. by applying a curing agent, such as heat and/or ultraviolet light.

If a mold 12 has been applied, the mold 12 may be removed prior to curing the first adhesive substance 16. Alternatively, the mold 12 may be left while curing the first adhesive substance 16, thereby fastening the mold 12 to the solid surface 6 and/or the identification tag 4.

In the example illustrated in FIG. 1, the first surface 8 and the solid surface 6 are attached together with a second adhesive substance 20. The second adhesive substance 20 may be liquid, plastic and/or pre-cured to attain a predetermined plasticity. After positioning the identification tag 4 with the first surface 8 and the solid surface 6 in contact with the second adhesive substance 20, the second adhesive substance 20 may be cured, or initially cured. However, in other exemplary assemblies, the second adhesive substance 20 may be cured at a later stage, e.g. concurrently with curing of the first adhesive substance 16.

Figure 2:
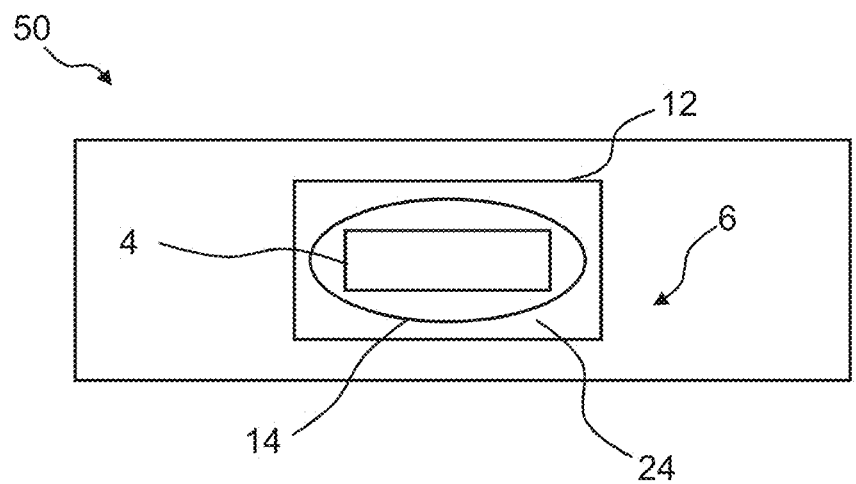
FIG. 2 schematically illustrates a top view of an exemplary step of a method.

FIG. 2 schematically illustrates a top view of an exemplary step 50 of the method. FIG. 2 illustrates the identification tag 4 being enclosed within the concave surface 14 of the mold 12. Further, FIG. 2 illustrates that the mold 12 abuts a part 24 of the solid surface 6 circumscribing the identification tag 4.

Figure 3:
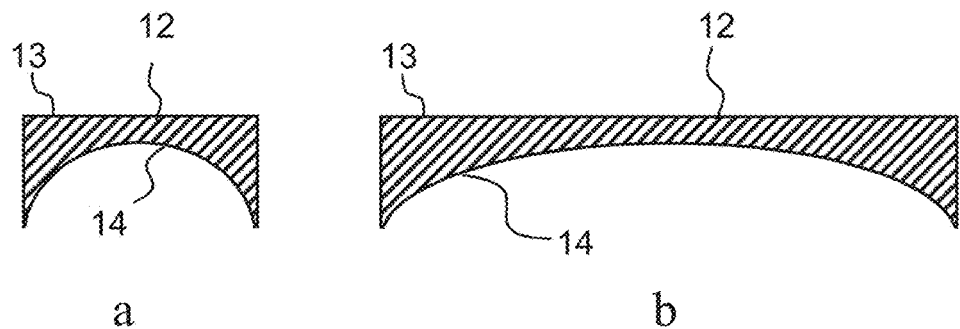
FIG. 3 schematically illustrates a cross section of an exemplary mold.

FIG. 3 schematically illustrates a cross section of an exemplary mold 12. An identification tag 4 may be an elongated body as also shown in FIG. 1 and FIG. 2.

Hence, the mold 12 may accordingly be an elongated body. FIG. 3*a* shows an end cross sectional view of the mold 12. FIG. 3*b* shows a side cross sectional view of the mold 12. The mold 12 comprises an outer surface 13 and a concave surface 14. The concave surface 14 is configured to shape the first adhesive substance 16 as described in relation to FIG. 1. The concave surface 14 is formed as part of an ellipse.

Figure 4:
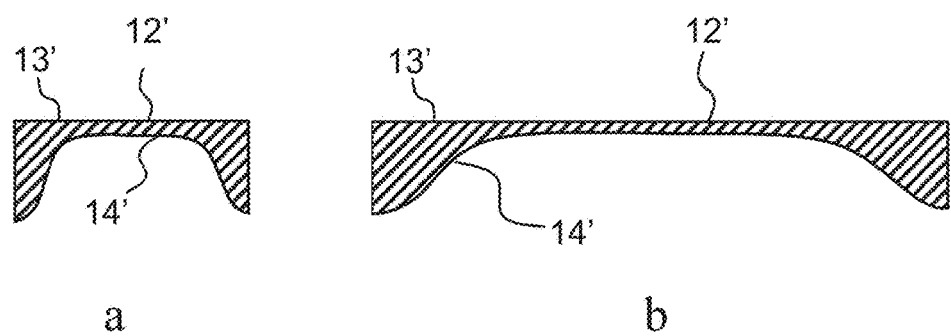
FIG. 4 schematically illustrates a cross section of an exemplary mold.

FIG. 4 schematically illustrates a cross section of an exemplary mold 12'. FIG. 4*a* shows an end cross sectional view of the mold 12'. FIG. 4*b* shows a side cross sectional view of the mold 12'. The mold 12' comprises an outer surface 13' and a concave surface 14'. The concave surface 14' is differently shaped than the elliptical concave surface 14 of FIG. 3. The concave surface 14' is shaped to form a slope near the circumference of the concave surface 14' that is close to zero.

Figure 5:
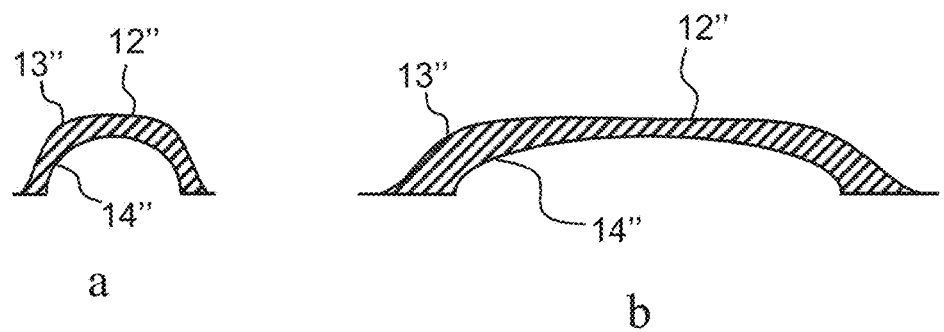
FIG. 5 schematically illustrates a cross section of an exemplary mold.

FIG. 5 schematically illustrates a cross section of an exemplary mold 12". FIG. 5*a* shows an end cross sectional view of the mold 12". FIG. 5*b* shows a side cross sectional view of the mold 12". The mold 12' comprises an outer surface 13" and a concave surface 14". The outer surface 13" is shaped to form a smooth cover surface. The concave surface 14" is adapted to fit the identification tag 4 to be attached to the solid surface 6.

Figure 6:
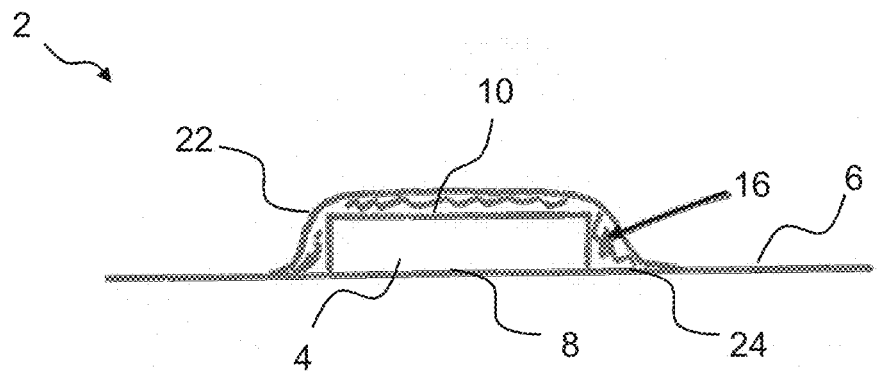
FIG. 6 schematically illustrates an exemplary assembly.

FIG. 6 schematically illustrates an exemplary assembly 2. The assembly 2 comprises an identification tag 4, a solid surface 6 and a first adhesive substance 16. The identification tag 4 comprises a first surface 8 and a second surface 10. The second surface 10 is opposite the first surface 8. The first surface 8 is facing the solid surface 6.

A predetermined amount of the first adhesive substance 16 has been formed to cover the identification tag 4 and a part 24 of the solid surface 6 circumscribing the identification tag 4. The identification tag 4 is thereby completely enclosed by the first adhesive substance 16 and the solid surface 6. The first adhesive substance 16 further adhere to the solid surface 6 and the first adhesive substance 16 and the identification tag 4 is thereby attached to the solid surface 6 when the first adhesive substance 16 is cured. Curing of the first adhesive substance 16 further forms a hard and smooth cover surface 22.

The shape of the cover surface 22 serves to deflect a possible impact e.g. from another instrument during washing, thereby improving the strength of the attachment of the identification tag 4 to the solid surface 6. Further, the shape of the cover surface is smooth, i.e. without irregularities, edges which may tear plastic gloves are thereby avoided.

Figure 7:
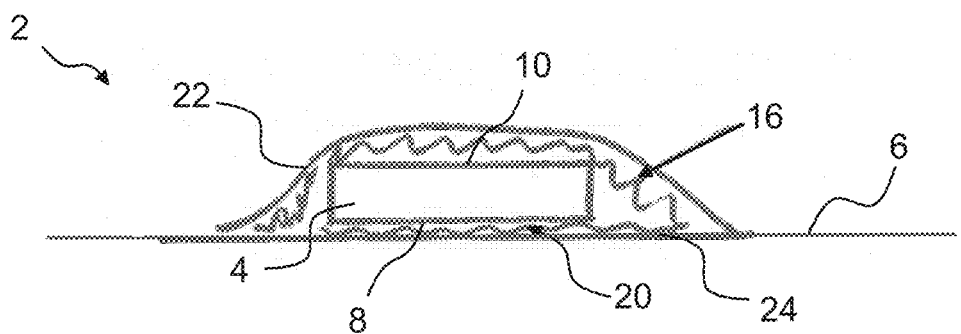
FIG. 7 schematically illustrates an exemplary assembly comprising a second adhesive substance.

FIG. 7 schematically illustrates an exemplary assembly 2. The exemplary assembly 2 as illustrated in FIG. 7 comprises the same features as the assembly 2 illustrated in FIG. 6. However, the assembly 2 of FIG. 7 further comprises a second adhesive substance 20 between the first surface 8 of the identification tag 4 and the solid surface 6. The second adhesive substance 20 may add to the strength of the attachment of the identification tag 4 to the solid surface 6. Furthermore, the second adhesive substance 20 may initially be cured prior to applying the first adhesive substance 16, thereby providing for an improved automated process of attaching and covering the identification tag, since movement of the identification tag 4 relative to the solid surface 6 when applying the first adhesive substance 16 may be prevented.

Figure 8:
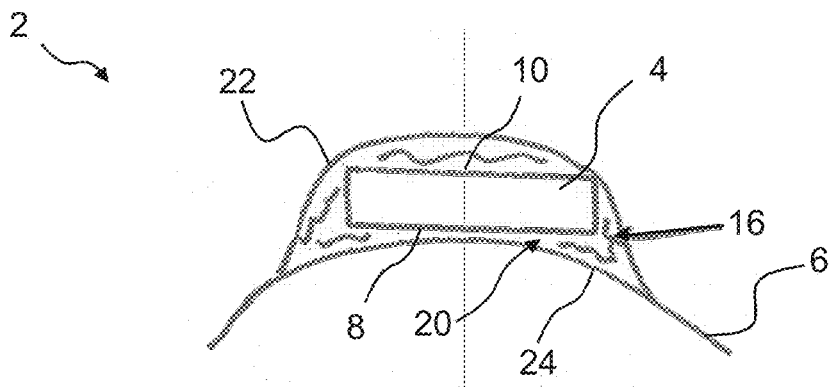
FIG. 8 schematically illustrates an exemplary assembly wherein the s id surface is not plane.

FIG. 8 schematically illustrates an exemplary assembly 2 wherein the solid surface 6 is non planar. To account for the non planar solid surface 6, if a mold is used for forming the first adhesive substance 16, the mold may be fitted to the shape of the solid surface 6.

It is seen in FIG. 8 that the first adhesive substance 16 and the second adhesive substance 20 create a support for the identification tag 4. Further, the first adhesive substance 16 and the second adhesive substance 20 fill out grooves between the identification tag 4 and the solid surface 6. The absence of grooves between the identification tag 4 and the solid surface 6 results in less risk of the identification tag 4 being separated from the solid surface upon an impact. Further, germs will not accumulate in the grooves. An even further advantage is that the identification tag 4 does not provide sharp edges that may potentially rip or tear plastic gloves.

The cover surface 22 cover the identification tag 4 and intersect with a part 24 of the solid surface 6 circumscribing the identification tag 4 as also illustrated in FIG. 2.

In the above illustrations, the identification tag 4 has been depicted as a solid elongated element. However, the identification tag 4 may be any other shape, soft and/or bendable.

Figure 9:
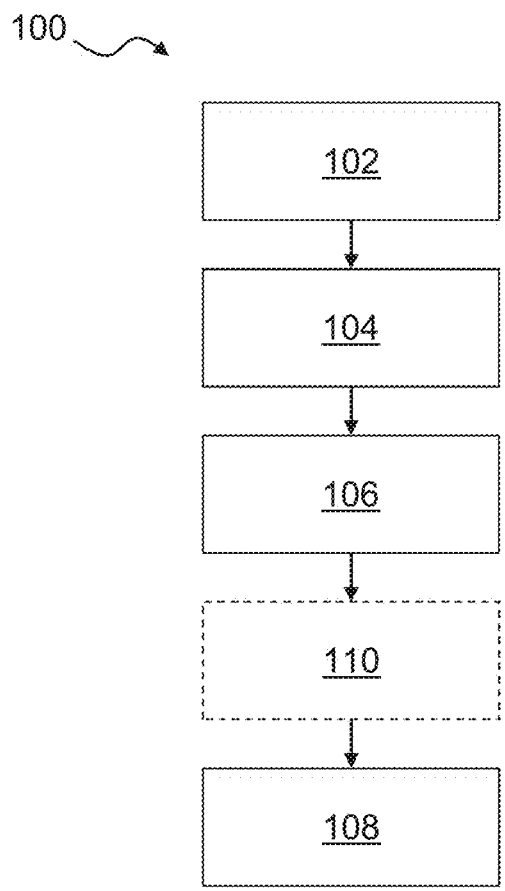
FIG. 9 shows an exemplary flow diagram of a method.

FIG. 9 shows a flow diagram of an exemplary method 100 for attaching an identification tag to a solid surface and protecting the identification tag.

The method 100 comprises positioning a first surface of the identification tag in contact with the solid surface 102. The identification tag further has a second surface opposite the first surface.

The method 100 further comprises applying a predetermine among of a first adhesive substance on the second surface 104 after positioning the first surface in contact with the solid surface 102. The first adhesive substance is plastic and/or liquid and/or viscous, such that it can be formed to form a desired shape. The first adhesive substance is further curable, such that it can be hardened to change from a viscous, liquid or plastic material to a hard material that is not easily deformed.

The method 100 further comprises forming the first adhesive substance 106 after applying the first adhesive substance on the second surface 104, such that the first adhesive substance covers the identification tag and abut a part of the solid surface circumscribing the identification tag. Forming the first adhesive substance 106 may for example comprise applying a concave surface of a mold to a part of the solid surface. The concave surface may be applied such that the mold abuts a part of the solid surface circumscribing the identification tag. Thereby, the concave surface is applied over the identification tag and the identification tag is enclosed between the concave surface of the mold and the solid surface. Applying the concave surface over the identification tag furthermore results in spreading the first adhesive substance over the identification tag. Alternatively or additionally, forming the first adhesive substance may comprise subjecting the first adhesive substance to a first energy intensity for a first duration. The first energy intensity and the first duration may be selected such that viscosity of the first adhesive substance is decreased relative to a viscosity of the first adhesive substance when applied to the second surface.

Subsequently to forming the first adhesive substance 106, the method 100 comprises curing of the first adhesive substance 108. The curing of the first adhesive substance 108 hardens the first adhesive substance and permanently fastens the first adhesive substance to the identification tag and the solid surface.

Optionally, if forming the first adhesive substance 106 comprises applying a concave surface of a mold, the method 100 may comprise removing the mold 110 prior to curing the first adhesive substance 108.

The method 100 may optionally comprise constructing the mold. Construction of the mold may be performed before positioning the first surface of the identification tag in contact with the solid surface 102. However, construction of the mold may be performed at any point prior to applying the concave surface over the identification tag.

The method 100 may optionally comprise applying a second adhesive substance between the first surface of the identification tag and the solid surface. Positioning the first surface of the identification tag in contact with the solid surface 102, may comprise applying the second adhesive substance between the first surface and the solid surface. Further, the method 100 may comprise pre-curing the second adhesive substance prior to applying the second adhesive substance between the first surface and the solid surface. Pre-curing of the second adhesive substance may improve managing the second adhesive substance to not flow excessively. Thereby, the second adhesive substance may remain between the first surface and the solid surface.

Prior to applying a concave surface of a mold, the method 100 may comprise coating the concave surface with a substance that prevents or at least avert the first adhesive substance from adhering to the concave surface. Hence, the mold may be reusable.

Generally, some steps of the method may be interchanged. Especially the steps of positioning the first surface in contact with the solid surface, applying the first adhesive substance on the second surface and applying a concave surface of a mold to a part of the solid surface may be interchanged.

Figure 10:
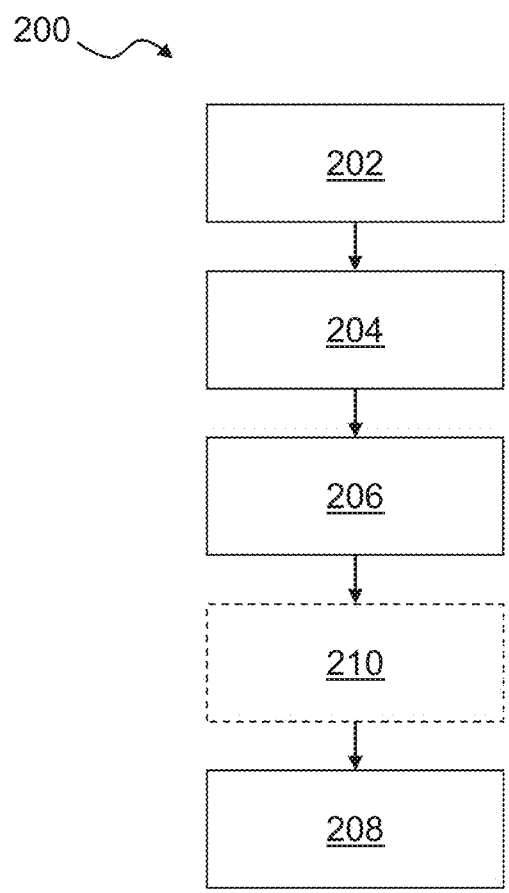
FIG. 10 shows an exemplary flow diagram of a method.

FIG. 10 shows a flow diagram of an exemplary method 200 for attaching an identification tag to a solid surface and protecting the identification tag. The identification tag comprises a first surface and a second surface opposite the first surface.

The method 200 comprises applying a first adhesive substance on the second surface 202 by applying the first adhesive substance to a concave surface of a mold, and positioning the identification tag in the cavity formed by the concave surface of the mold, such that the second surface of the identification tag face the concave surface of the mold. Thereby the first adhesive substance is applied to the second surface of the identification tag. The mold is formed to fit the identification tag, and the solid surface. Applying the first adhesive substance to the second surface of the identification tag 202 may imply filling the cavity formed by the concave surface of the mold with the first adhesive substance and immersing the identification tag in the first adhesive substance. The identification tag may be completely submerged in the first adhesive substance.

After applying the first adhesive substance on the second surface 202, the method 200 further comprises applying the concave surface of the mold to the solid surface 204 such that the mold abuts a part of the solid surface. Given that the identification tag is positioned in the cavity formed by the concave surface of the mold, application of the mold to the solid surface 204 causes subsequently that the first surface of the identification tag is positioned contact with the solid surface 206, and that the mold abuts a part of the solid surface circumscribing the identification tag.

Subsequently to positioning the first surface of the identification tag in contact with the solid surface 206, the method 200 comprises curing of the first adhesive substance 208. The curing of the first adhesive substance 208 hardens the first adhesive substance and permanently fastens the first adhesive substance to the identification tag and the solid surface.

Optionally, the method 200 may comprise removing the mold 210 prior to curing the first adhesive substance 208. Removing the mold 210 may comprise turning the assembly comprising the solid surface, the mold and the identification tag upside down, to leave the identification tag and the first adhesive substance on the solid surface. Other solutions may be proposed to account for this problem, e.g. a centrifugal movement.

Generally the method may comprise turning and reorientation of the parts, e.g. the solid surface, the identification tag, the mold etc. turning or reorientation may assist in causing desired interrelating adhering, arranging and/or positioning of parts.

If the optional step of removing the mold 210 is omitted, the mold is fastened to the solid surface and/or the identification tag by curing of the first adhesive substance 208. Thereby, the mold forms a cover surface covering and protecting the identification tag.

Figure 11:
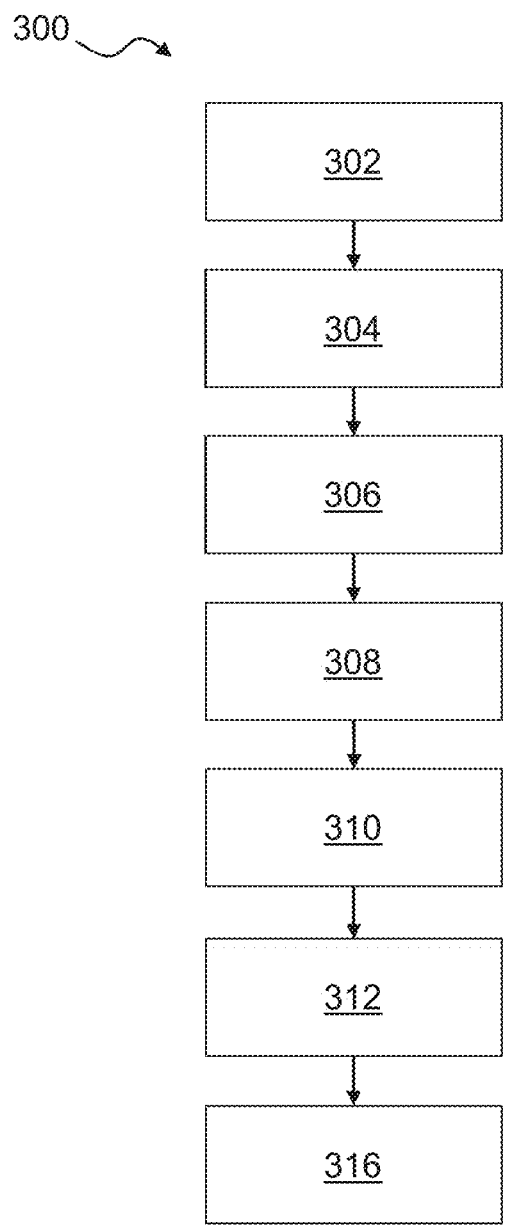
FIG. 11 shows a flow diagram of an exemplary method.

FIG. 11 shows a flow diagram of steps of an exemplary method 300 for attaching an identification tag to a solid surface and protecting the identification tag. The identification tag comprises a first surface and a second surface opposite the first surface. The method 300 comprises identifying an attachment site on the solid surface 302; applying a second adhesive substance 304; positioning the first surface of the identification tag in contact with an attachment site of the solid surface 306; initially curing the second adhesive substance 308; applying a predetermined amount of a first adhesive substance on the second surface 310; forming the first adhesive substance 312; and curing the first adhesive substance 316.

Identification of the attachment site 302 may comprise recognition of the solid surface, such as recognition of e.g. the instrument comprising the solid surface. Recognition of the solid surface may be such as optical recognition, such as image recognition and/or such as pattern recognition. Identification of the attachment site 302 may further comprise a table lookup and/or a database lookup for the recognized solid surface, wherein the table and/or database comprise attachment site data of the solid surface. The attachment site data may comprise instructions for providing the attachment site on the solid surface.

Applying a second adhesive substance 304 may comprise applying the second adhesive substance to the solid surface, such as applying the second adhesive substance to the identified attachment site of the solid surface. Alternatively, the second adhesive substance may be applied to the first surface of the identification tag.

Positioning the first surface of the identification tag in contact with the solid surface 306 may comprise positioning the first surface of the identification tag at the identified attachment site of the solid surface. Furthermore, the positioning of the first surface of the identification tag in contact with the solid surface 306 may be provided with the second adhesive substance in between the first surface and the solid surface. Provision of the second adhesive substance in between the first surface and the solid surface may be provided by the prior application of the second adhesive substance 304.

Initially curing the second adhesive substance 308 may comprise applying a curing agent, such as heat and/or ultraviolet radiation, to the second adhesive substance. Initially curing the second adhesive substance 308 may comprise curing of the second adhesive substance for an initial duration. Initially curing the second adhesive substance 308 may be enough to provide immobilization of the identification tag relative to the solid surface, e.g. immobilization of the identification tag such that remaining steps of the method 300 may be performed without moving the identification tag. The initial duration may be less than 30 seconds, such as less than 10 seconds, such as less than 5 seconds, such as less than 2 seconds, such as less than 1 second.

Forming the first adhesive substance 312 may comprise forming the first adhesive substance such such that the first adhesive substance covers the identification tag and abuts a part of the solid surface circumscribing the identification tag. Alternatively or additionally, forming the first adhesive substance 312 may comprise applying a concave surface of a mold over the identification tag, such that the mold abuts a part of the solid surface circumscribing the identification tag. The mold may be positioned such that the identification tag is positioned in the cavity formed by the concave surface of the mold. The mold may subsequently be removed.

After forming the first adhesive substance 312, the first adhesive substance is cured 316. Curing of the first adhesive substance 316 may comprise applying a curing agent, such as heat and/or ultraviolet radiation, to the first adhesive substance. Curing the first adhesive substance 316 may comprise curing of the first adhesive substance for a first duration. The first duration may be longer than the initial duration. The first duration may be more than 30 seconds, such as more than 60 seconds, such as more than 5 minutes, such as more than 10 minutes, such as more than 30 minutes, such as 60 minutes. Curing of the first adhesive substance 316 may further comprise concurrent curing of the second adhesive substance. Curing of the second adhesive substance may comprise applying a curing agent, such as heat and/or ultraviolet radiation, to the second adhesive substance.

One or more of the steps of the method 300 as described may optionally be omitted, either independently or collectively. For example, the step of identifying the attachment site on the solid surface 302, and/or the step of applying a second adhesive substance 304, and/or the step of initially curing the second adhesive substance 308, may be omitted.

Figure 12:
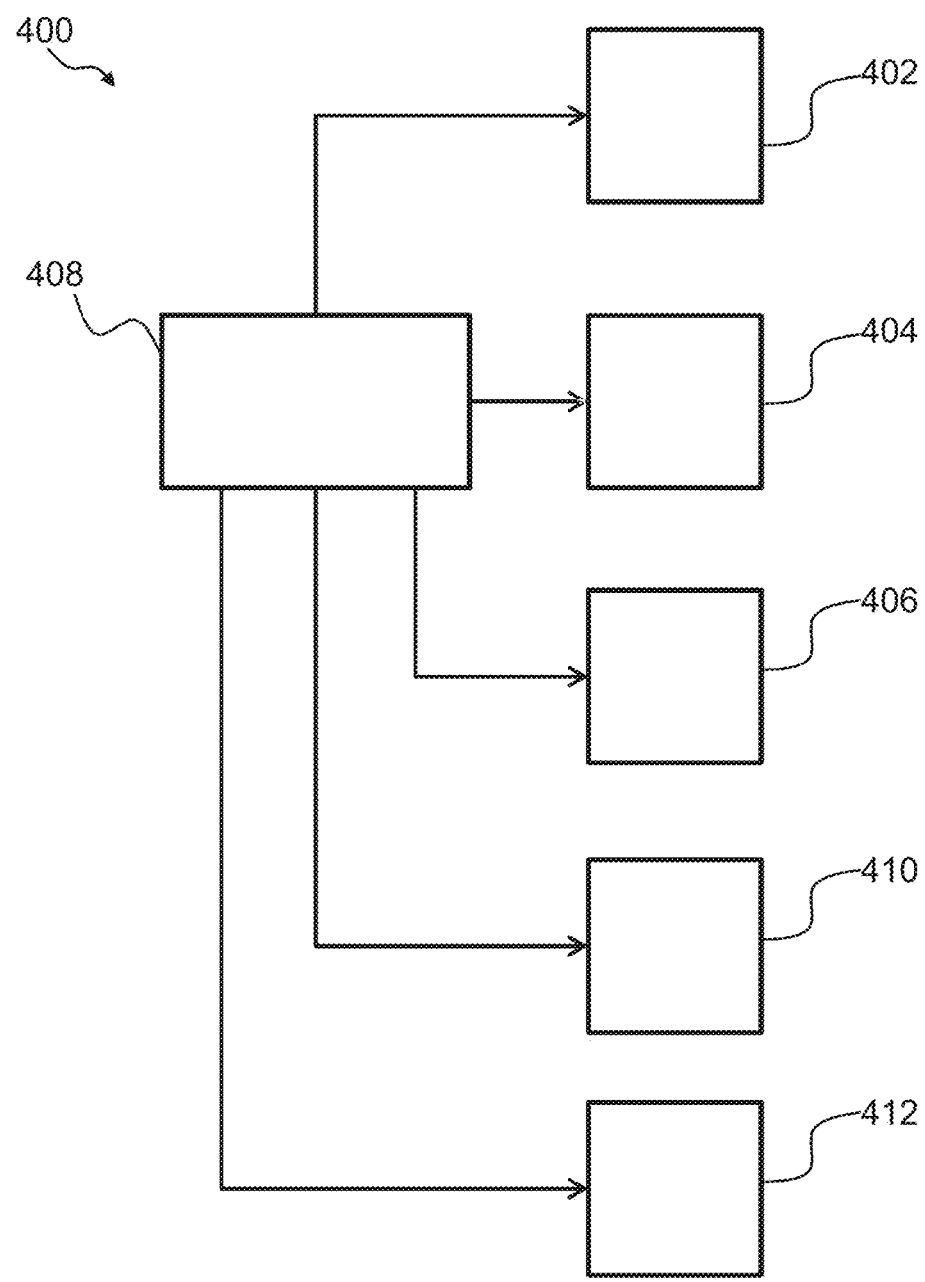
FIG. 12 schematically illustrates an exemplary apparatus.

FIG. 12 schematically shows an exemplary apparatus 400 for attaching an identification tag to a solid surface.

The apparatus 400 comprise positioning means 402, application means 404, forming means 406, curing means 410 and control means 408.

The positioning means 402 is configured to position the first surface of the identification tag in contact with the solid surface. The positioning means 402 may be a robotic arm, such as a first robotic arm. The positioning means 402 may further be configured to apply a second adhesive substance between the solid surface and the first surface.

The application means 404 is configured to apply a predetermined amount of the first adhesive substance on a second surface of the identification tag. The application means 404 may be a robotic arm, e.g. a second robotic arm or the first robotic arm.

The forming means 406 may comprise a robotic arm, e.g. a third robotic arm, the second robotic arm, or the first robotic arm. The forming means 406 may comprise heating means and/or viscosity alteration means. The forming means 406 are configured to form the first adhesive substance such that the first adhesive substance covers the identification tag and abut a part of the solid surface circumscribing the identification tag.

The control means 408 may comprise a control unit, such as a processing unit, configured to control a curing process, such as an initial curing of the second adhesive substance and/or the curing process of the first adhesive substance and/or optionally the second adhesive substance.

The control means 408 may be configured to control the timing of the curing process and/or the application of a curing agent, such as heat and/or ultraviolet radiation.

The control means 408 is connected to the positioning means 402, the application means 404, the forming means 406, and the curring means 410. The control means 408 is configured to control the positioning means 402, the application means 404, the forming means 406, and the curring means 410.

Optionally, the apparatus 400 comprises identification means 412 configured to identify an attachment site on the solid surface for positioning of the first surface of the identification tag. The identification means 412 may comprise a camera.

The control means 408 may be configured to control the curing means 410 to initially cure the second adhesive substance after positioning of the first surface of the identification tag in contact with the solid surface by the positioning means 402, and before the application means 404 have applied the first adhesive substance.

The control means 408 is further configured to control the curing means 410 to cure the first adhesive substance after the forming means 406 have formed the first adhesive substance.

In another exemplary apparatus (not shown), one or more of the positioning means 402, the application means 404, the forming means 406, the curing means 410, and the identification means 412, may be integrated into a single unit, such as a first robotic arm.

Methods, apparatuses, and assemblies are disclosed in the following items:

Item 1. A method of attaching an identification tag to a solid surface and protecting the identification tag, the identification tag having a first surface and a second surface opposite the first surface, the method comprising:
- positioning the first surface of the identification tag in contact with the solid surface, wherein positioning the first surface of the identification tag in contact with the solid surface comprises applying a second adhesive substance between the solid surface and the first surface;
- initially curing the second adhesive substance;
- applying a first adhesive substance on the second surface, the first adhesive substance being plastic during application and curable;
- applying a concave surface of a mold such that the mold abuts a part of the solid surface circumscribing the identification tag; and
- curing the first adhesive substance.

Item 2. Method according to item 1, wherein the second adhesive substance is the same type of adhesive substance as the first adhesive substance.

Item 3. Method according to any of items 1 or 2, wherein curing the first adhesive substance further comprises curing the second adhesive substance.

Item 4. Method according to any of the preceding items, wherein initially curing the second adhesive substance has a second duration of less than 1 second.

Item 5. Method according to any of the preceding items, wherein the mold is shaped to fit the combination of the identification tag and the solid surface.

Item 6. Method according to any of the preceding items, wherein applying the first adhesive substance comprises applying a predetermined amount of the first adhesive substance.

Item 7. Method according to any of the preceding items, wherein the method comprises coating the concave surface of the mold with a substance to prevent the first adhesive substance to adhere to the concave surface.

Item 8. Method according to any of the preceding items, wherein the curing of the first adhesive substance and/or curing of the second adhesive substance is performed by applying heat and/or ultraviolet light to the first adhesive substance and/or the second adhesive substance, respectively.

Item 9. Method according to any of the preceding items, wherein the first adhesive substance is an epoxy glue.

Item 10. Method according to any of the preceding items, wherein the solid surface is a solid surface of a medical instrument, such as a surgical instrument, such as a lancet or a scissor or a clamp.

Item 11. Method according to any of the preceding items, wherein initially curing the second adhesive substance has a second duration less than a first duration of curing the first adhesive substance.

Item 12. Method according to any of the preceding items, wherein the method comprises identifying an attachment site on the solid surface for positioning the first surface of the identification tag.

Item 13. An apparatus for attaching an identification tag to a solid surface and protecting the identification tag, wherein the apparatus comprises:
- positioning means configured to position the first surface of the identification tag in contact with the solid surface, wherein positioning of the first surface of the identification tag in contact with the solid surface comprises applying a second adhesive substance between the solid surface and the first surface;
- means to apply a first adhesive substance on the second surface, the first adhesive substance being plastic during application and curable;
- means to apply a concave surface of a mold such that the mold abuts a part of the solid surface circumscribing the identification tag; and
- control means configured to initially cure the second adhesive substance after positioning of the first surface of the identification tag in contact with the solid surface, and configured to cure the first adhesive substance.

Item 14. Apparatus according to item 13, wherein the control means are configured to initially cure the second adhesive substance with a second duration of less than 1 second.

Item 15. Apparatus according to any of items 13 or 14, wherein the apparatus comprises identification means configured to identify an attachment site on the solid surface for positioning of the first surface of the identification tag.

Item 16. A method of attaching an identification tag to a solid surface and protecting the identification tag, the identification tag having a first surface and a second surface opposite the first surface, the method comprising:
- positioning the first surface of the identification tag in contact with the solid surface;
- applying a first adhesive substance on the second surface, the first adhesive substance being plastic during application and curable;
- applying a concave surface of a mold such that the mold abuts a part of the solid surface circumscribing the identification tag; and
- curing the first adhesive substance.

Item 17. Method according to item 16, wherein positioning the first surface of the identification tag in contact with the solid surface comprise applying a second adhesive substance between the solid surface and the first surface.

Item 18. Method according to item 17, wherein the second adhesive substance is the same type of adhesive substance as the first adhesive substance.

Item 19. Method according to any of items 17 or 18, wherein the second adhesive substance and the first adhesive substance cure concurrently.

Item 20. Method according to any of items 17-19, wherein the second adhesive substance is pre-cured prior to applying the second adhesive substance between the solid surface and the first surface.

Item 21. Method according to any of items 16-20, wherein the mold fits the identification tag and the solid surface.

Item 22. Method according to any of items 16-21, wherein application of the first adhesive substance comprises applying a predetermined amount of the first adhesive substance.

Item 23. Method according to any of items 16-22, wherein the concave surface of the mold is coated with a substance to prevent the first adhesive substance to adhere to the concave surface.

Item 24. Method according to any of items 16-23, wherein the curing of the first adhesive substance is performed by applying heat to the first adhesive substance.

Item 25. An assembly comprising:
- a solid surface;

an identification tag attached to the solid surface, the identification tag having a first surface and a second surface opposite the first surface, the first surface facing the solid surface;
a first adhesive substance covering the second surface and a part of the solid surface circumscribing the identification tag;
wherein the first adhesive substance is a plastic and curable material.

Item 26. Assembly according to item 25, wherein a second adhesive substance is applied between the solid surface and the first surface, the second adhesive substance being same type of adhesive substance as the first adhesive substance.

Item 27. Assembly according to any of items 25 or 26, wherein the first adhesive substance is an epoxy glue.

Item 28. Assembly according to any of items 25-27, wherein the solid surface is a solid surface of a medical instrument, such as a surgical instrument, such as a lancet or a scissor or a clamp.

Item 29. Assembly according to any of items 25-28, wherein a cover surface is covering the second surface and a part of the solid surface circumscribing the identification tag, and wherein the cover surface is hard and smooth.

Item 30. Assembly according item 29, wherein the first adhesive substance forms the cover surface when the first adhesive substance has been cured.

LIST OF REFERENCES 2 assembly
4 identification tag
6 solid surface
7 attachment site
8 first surface
10 second surface
12, 12', 12" mold
13, 13', 13" outer surface
14, 14', 14" concave surface
16 first adhesive substance
18 applying the mold
20 second adhesive substance
22 cover surface
50 step of a method
100 method
102 positioning the identification tag
104 applying a first adhesive substance
106 forming the first adhesive substance
108 curing the first adhesive substance
110 removing the mold
200 method
206 positioning the identification tag
202 applying a first adhesive substance
204 applying a concave surface of a mold
208 curing the first adhesive substance
210 removing the mold
300 method
302 identifying an attachment site
304 applying a second adhesive substance
306 positioning the identification tag
308 initially curing the second adhesive substance
310 applying a first adhesive substance
312 forming the first adhesive substance
316 curing the first adhesive substance
400 apparatus
402 positioning means
404 application means
406 forming means
408 control means
410 curing means
412 identification means

The invention claimed is:

1. A method for attaching an identification tag to a solid surface and protecting the identification tag, the identification tag including a first surface and a second surface opposite the first surface, the method comprising:
    positioning the first surface of the identification tag in contact with an attachment site of the solid surface;
    applying a predetermined amount of a first adhesive substance on the second surface, the first adhesive substance comprising plastic during application and curable after application, the first adhesive substance including a first viscosity at a time of application;
    forming the first adhesive substance, such that the first adhesive substance covers the identification tag and abuts a part of the solid surface circumscribing the identification tag; and
    curing the first adhesive substance,
    wherein forming the first adhesive substance comprises applying a concave surface of a mold such that the mold abuts a part of the solid surface circumscribing the identification tag.

2. The method of claim 1, wherein the solid surface is a solid surface of a medical instrument able to withstand repeated sterilization procedures at high temperature.

3. The method of claim 1, wherein forming the first adhesive substance comprises subjecting the first adhesive substance to a first energy intensity for a first duration, wherein the first energy intensity and the first duration are selected such that viscosity of the first adhesive substance is decreased relative to the first viscosity.

4. The method of claim 3, wherein the first energy intensity is a constant temperature.

5. The method of claim 3, wherein curing the first adhesive substance comprises subjecting the first adhesive substance to a second energy intensity for a second duration.

6. The method of claim 5, wherein the second energy intensity is similar to the first energy intensity.

7. The method of claim 5, wherein the second duration is more than 10 minutes.

8. The method of claim 1, wherein viscosity of the first adhesive substance initially decreases and subsequently increases relative to the first viscosity when subjecting the first adhesive substance to a first energy intensity.

9. The method of claim 1, wherein positioning the first surface of the identification tag in contact with the solid surface comprises applying a second adhesive substance between the solid surface and the first surface.

10. The method of claim 1, wherein positioning the first surface of the identification tag in contact with the solid surface comprises initially curing the second adhesive substance.

11. The method of claim 10, wherein initially curing the second adhesive substance has an initial duration of less than 1 second.

12. The method of claim 10, wherein initially curing the second adhesive substance comprises applying heat and/or radiation to the second adhesive substance.

13. The method of claim 9, wherein:
    the second adhesive substance is the same type of adhesive substance as the first adhesive substance;
    positioning the first surface of the identification tag includes positioning using a first robotic arm; and applying the predetermined amount of the first adhesive substance includes applying using a second robotic arm and/or the first robotic arm, wherein the first adhesive substance includes a first liquid adhesive substance.

14. The method of claim 1, wherein forming the first adhesive substance comprises removing the mold.

15. The method of claim 1, wherein forming the first adhesive substance comprises selecting the mold to fit the combination of the identification tag and the solid surface.

16. The method of claim 1, wherein the concave surface of the mold is coated with a substance to prevent the first adhesive substance to adhere to the concave surface.

17. The method of claim 1, wherein the first adhesive substance is an epoxy glue.

18. The method of claim 1, wherein the solid surface is a metal surface.

19. The method of claim 1, wherein the method comprises identifying the attachment site.

20. The method of claim 1 further comprising preparing the attachment site, wherein preparing the attachment site substantially does not alter the solid surface.

21. The method of claim 1, wherein forming the first adhesive substance comprises forming the first adhesive substance using a robotic arm.

* * * * *